United States Patent [19]
Solomon

[11] Patent Number: 5,880,812
[45] Date of Patent: Mar. 9, 1999

[54] METHOD AND APPARATUS FOR EVALUATING AND MAPPING VISUAL FIELD

[75] Inventor: Arieh Solomon, Tel-Aviv, Israel

[73] Assignee: Ramot-University Authority for Applied Research and Industrial Development, Ltd., Israel

[21] Appl. No.: 816,553

[22] Filed: Mar. 13, 1997

[51] Int. Cl.$^6$ .................................................. A61B 3/14
[52] U.S. Cl. .......................... 351/210; 351/209; 351/246
[58] Field of Search .................................. 351/209, 210, 351/246, 247, 205, 206, 200

[56] References Cited

U.S. PATENT DOCUMENTS

| | | |
|---|---|---|
| 3,827,789 | 8/1974 | Molner et al. . |
| 4,012,128 | 3/1977 | Regan . |
| 4,059,348 | 11/1977 | Jernigan . |
| 4,255,022 | 3/1981 | Kuether et al. . |
| 4,255,023 | 3/1981 | House . |
| 4,626,090 | 12/1986 | Charlier et al. ........................ 351/226 |
| 4,679,917 | 7/1987 | Genco et al. ........................... 351/243 |
| 4,702,576 | 10/1987 | Magnante ............................... 351/214 |
| 4,711,542 | 12/1987 | Ichihashi et al. ....................... 351/221 |
| 4,776,687 | 10/1988 | Nakanishi et al. ..................... 351/214 |
| 4,781,453 | 11/1988 | Kobayashi ............................. 351/205 |
| 4,832,043 | 5/1989 | Ichihashi ................................ 128/745 |
| 4,852,987 | 8/1989 | Lohmann ............................... 351/221 |
| 4,854,692 | 8/1989 | Kobayashi ............................. 351/221 |
| 4,863,267 | 9/1989 | Flammer ................................ 351/221 |
| 4,927,259 | 5/1990 | Weber .................................... 351/224 |
| 4,993,827 | 2/1991 | Benedek et al. ....................... 351/221 |
| 5,203,328 | 4/1993 | Samuels et al. ........................ 128/633 |
| 5,231,674 | 7/1993 | Cleveland et al. . |
| 5,258,788 | 11/1993 | Furuya .................................. 351/221 |
| 5,270,748 | 12/1993 | Katz ...................................... 351/210 |
| 5,303,709 | 4/1994 | Dreher et al. .......................... 128/665 |
| 5,311,225 | 5/1994 | Acier et al. ............................ 351/221 |
| 5,341,181 | 8/1994 | Godard .................................. 351/210 |

FOREIGN PATENT DOCUMENTS 195 05 399
A1   2/1995   Germany .

OTHER PUBLICATIONS

Eye Tracking Systems Handbook, from the Applied Science Laboratories Company, Bedford, Massachusetts.

Harrington, in The Visual Fields, third edition, The C.V. Mosby Co., Saint Louis, MO, 1971, Section 10, select pages only.

*Primary Examiner*—Hung Xuan Dang
*Attorney, Agent, or Firm*—Kohn & Associates

[57] ABSTRACT

A method for examining a visual field of a subject includes the steps of stimulating the subject eye movement reflex to an off field visual stimulus and mapping the subject visual field based on a positive reflex to the stimulus. An apparatus (20) for evaluating the visual field of a subject (22) includes a subject affixation mechanism (24) for affixing a portion of the apparatus (20) to the subject (22), an eye tracking mechanism (26) operatively connected to the subject affixation means (24) for tracking eye movement of the subject (22), and visual field stimulus generater (28) operatively connected to the affixation mechanism (24) for generating a visual stimulus.

14 Claims, 1 Drawing Sheet

METHOD AND APPARATUS FOR EVALUATING AND MAPPING VISUAL FIELD

TECHNICAL FIELD

The present invention relates to a method and apparatus for visual field testing. More particularly, the present invention relates to a method and apparatus for assessing the visual field of a subject which utilizes the basic human reflex of eye movement towards a target entering a subject's field of vision.

BACKGROUND OF THE INVENTION

The measurement of a subject's visual field or visual field examination is one of the most basic and widely used tests in ophthalmology. The measurement of a subject's visual field is important in the diagnosis and assessment of various diseases or conditions including glaucoma and those neurological diseases which affect the visual system and brain.

A visual field is generally defined as the portion of space in which objects are simultaneously visible to the steadily fixating eye. Abstractly, the visual field can be thought of as somewhat more than one half of a hollow sphere situated before and around each eye of a subject. Within this portion of the sphere, objects are perceived while the eye is fixating, on a stationary point on the inner surface of the sphere. Objects that are visible on the inner surface of this portion of the sphere stimulate various portions of the retina and are then conducted through nerve fiber bundles and eventually stimulate the visual cortex of the brain. Visual field testing can reveal the amount of damage created by trauma or disease along the visual pathway from the retina to the visual center in the brain.

Traditional methods of testing and measuring visual field have required a great deal of concentration from the subject being tested. The test subject was required to subjectively respond, either visually, physically, or by means of an indicating device, that he has or has not sighted a target at a particular location in his visual field.

The delay between stimulation of the retina and the response of the person being tested results in a loss of spontaneity and creates both false positive and false negative results. The traditional methods of testing and measuring visual field require the subject to fixate on a central point while an examiner either moves objects through the subject's field of vision or various lights or stimuli would be presented within the subject's field of vision to which the subject would be asked to respond to. From these methods, plots of the location of each point seen by the subject are obtained, from which, the subject's field of vision can be mapped.

The primary difficulty associated with these traditional methods of measuring a subject's visual field is that the subject is required to fixate or gaze toward a central fixation point while the stimuli are presented within the subject's visual field. This requirement that the subject must fixate or gaze on a central fixation point leads to a great deal of fatigue, inaccuracy, and lack of repeatability due to false-positive or false-negative responses due to the natural tendency or reflex of the human eye to move towards a new stimuli within its visual field. When a stimulus enters the visual field of a subject, the subject has a tendency to move their eyes toward the new stimulus and away from the central fixation point or reference point.

In order to overcome the uncertainties and difficulties in the foregoing testing techniques, attempts have been made to utilize the natural characteristic voluntary or involuntary eye movements which results when a target is presented to a subject within his visual field. Such methods and apparatuses are disclosed in U.S. Pat. No. 3,827,789 to Molner et al., issued Aug. 6, 1974, and U.S. Pat. No. 4,059,348 to Jernigan, issued Nov. 22. 1977. The Molner et al. patent describes a method and apparatus for measuring a subject's visual field by presenting a target consisting of a spot of light at a series of selected locations within the subject's visual field and monitoring and interpreting the subject's resulting eye movements and positions. However, the Molner et al. patent teaches that in order to ensure accurate test results, it is essential that the subject be looking directly at a known reference or central fixation point on a screen at the time that the target is presented to the subject on the screen. When a spot or dot of light suddenly appears, the subject's eyes respond to the sudden appearance of the dot of light by directing the gaze and fixating on that target.

The Molner et al. patent teaches an apparatus which is employed to measure the subject's visual field and to make a permanent photographic image thereof including the targets which the subject sees as determined by an eye movement monitor and its associated logic on circuitry. However, the method disclosed in the Molner et al. patent requires the subject to fixate on a central fixation point which, as described above, has certain disadvantageous properties associated therewith. Furthermore, the method disclosed in Molner et al. merely detects eye movement and not actually tracking the position and location of the eye in response to a stimulus. By relying only on eye movement as an indicator of those points or stimuli, the method disclosed in Molner et al. only allows for a yes or no answer regarding the subject's departure from the fixation point to a newly presented target stimulus without giving an actual anatomical point on the retina which has been stimulated thereby facilitating exact mapping of the retina and subject's visual field.

Therefore it would be advantageous and desirable to have a method and apparatus for evaluating the visual field of a subject which eliminates the disadvantages set forth above and which provides more accurate and versatile test data which may be used for other applications.

SUMMARY OF THE INVENTION AND ADVANTAGES

According to the present invention, there is provided an apparatus for evaluating the visual field of a subject including subject affixation means for affixing a portion of the apparatus to the subject, eye tracking means operatively connected to the subject affixation means for tracking the eye movement of the subject, and visual field stimulus generating means operatively connected to the affixation means for generating a visual stimulus.

Additionally, there is provided a method for examining a visual field of a subject which includes the steps of stimulating the subject eye movement reflex to an off field visual stimulus and mapping the subject visual field based on positive reflex to the stimulus.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
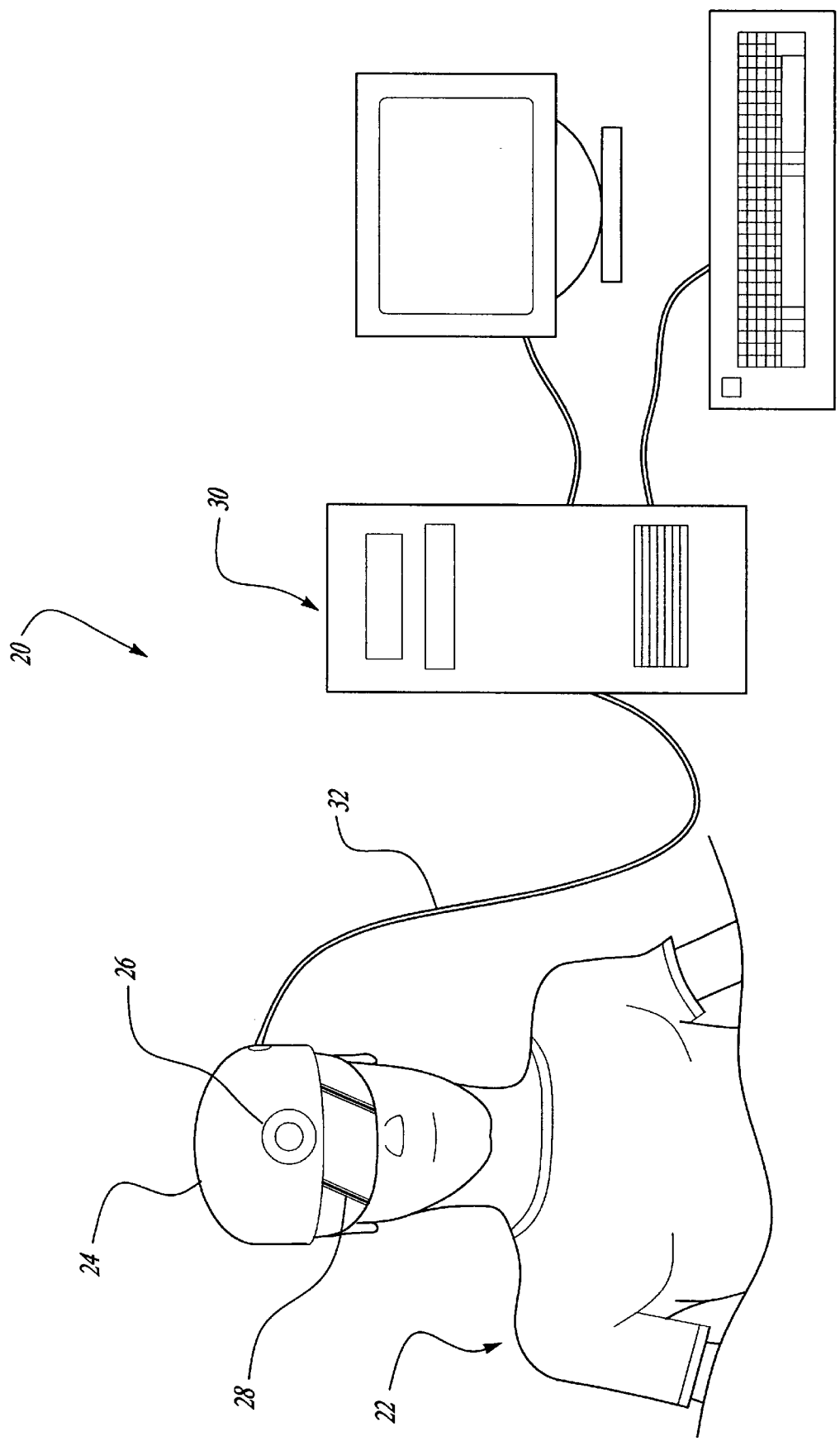
FIG. 1 is a schematic illustration of the present invention.

An apparatus adapted for evaluating the visual field of a subject 22 is generally shown at 20 in FIG. 1. The apparatus 20 includes subject affixation means 24 for affixing a portion of the apparatus 20 to the subject 22 and eye tracking means 26 operatively connected to the subject affixation means 24 for tracking eye movement of the subject 22. Visual field stimulus generating means 28 is operatively connected to the affixation means 24 for generating a visual stimulus.

More specifically, the apparatus 20 can also include data collection and analysis means 30 which is operatively connected to the apparatus 20 for collecting and analyzing data generated by the apparatus 20. The data collection and analysis means 30 can be operatively connected to the eye tracking means 26 and to the visual field stimulus generating means 28 by a 2-way transmission means 32 which provides for both the recording of eye movements of the subject 22 and for the transmission of input signals to the visual field stimulus generating means 28.

The apparatus 20 is designed to operate and take advantage of the basic reflex of a subject 22, such as a human, to direct the eye toward a stimulating target entering its field of vision.

The affixation means 24 for affixing at least a portion of the apparatus 20 to the subject 22 can include any suitable means of attaching at least a portion of the apparatus 20 to the subject 22. The subject affixation means 24 can include a helmet or headband-type device which is capable of being secured to the head of the subject 22. Preferably, the subject affixation means 24 is a helmet.

The eye tracking means 26 is preferably disposed on a forward portion of the helmet 24 and is capable of identifying and locating the point of gaze of the subject's eyes. The eye tracking means 26 can include head mounted optics such as an eye camera and/or illuminator attached to the helmet or headband worn by the subject. Such a camera can be used to measure the eye line of gaze with respect to the helmet or headband. Examples of such eye tracking means are set forth in the product literature "Eye Tracking Systems Handbook" from the Appllied Science Laboratories Company, Bedford, Mass., and is incorporated herein by reference. This type of eye movement measurement system is typically coupled with a control unit which may be coupled with a computer to process incoming eye data, calibrate the eye tracking system, record real-time data on disk, and perform off-line data analysis. The control unit, such as that supplied by Applied Science Laboratories, contains all of the electronics necessary for tracking eye movements.

The visual field stimulus generating means 28 which is operatively connected to the affixation means 24 is provided in order to generate a visual stimulus in the field of vision of the subject 22. In a preferred embodiment of the present invention, the visual field stimulus generating means 28 includes a visor 28 which can be attached to the helmet 24. The visor 28 is preferably a multi-media type device such as those commonly known as "virtual reality" visors common to the computer gaming industry. The visor 28 operates as a screen on which various target stimuli can be projected or generated. The visor is generally transparent, however, varying degrees of shading or tinting can be applied. The visor 28 which is operatively connected to the helmet 24 is also connected via a transmission means 32, typically in the form of a cable, to the data collection and analysis means 30.

Visors which can be used with the present invention can be obtained from Virtual Reality, Inc., NY, Virtual Research Systems, CA, Advanced Technology Systems, Inc., (N-Vision), VA, Artificial Reality Corp., CT, and Greenleaf Medical Systems, CA. The transmission means 32 can also include wireless data transmission in the form of infrared wireless data communication as is well known in the art.

The visual field stimulus generating means 28 in the form of the visor or "multi-media screen" allows for the generation of a portable visual field allowing the subject 22 to move their eyes toward a light target entering the visual field while at the same time looking in front of the visual field.

In operation, the helmet 24 having the eye tracking system 26 and visual field generating visor 28 attached thereto is placed upon the subject's head. The visual field stimulus generating visor 28 and the eye tracking system 26 are connected to the data generation, collection, and analysis means 30 through the transmission cable 32. The transmission cable 32 allows the flow of data both to and from the helmet 24. The subject data, generated as a result of eye movements of the subject 22 in response to target visual stimuli projected on the visual field stimulus generating visor 28, are collected and recorded by a computer, such as a standard personal computer, i.e., a P.C.

In conducting an actual examination of the visual field of a subject, the subject 22 looks in front of his visual field, as defined by the visual stimulus generating visor 28, toward a target which can be affixed on the visor or screen 28. While looking in front of his visual field, target light stimuli are generated on the visor or screen 28 from the computer 30. The subject's 22 eye movements in response to stimuli entering the subject's visual field are tracked by the eye tracking system 26 and are fed back to the computer 30 for analysis. A positive response to a visual stimulus is indicated by the detection of movement of the subject's eyes in response to the target stimuli projected onto the visor or screen 28 thus indicating a positive reflex to the stimulus.

The target stimuli projected onto the visor or screen 28 can be either static or can be kinetic. That is, the target stimuli projected onto the visor or screen 28 can be applied as a static or non-moving target or can be applied as a kinetic or moving target stimulus entering and/or exiting the field of vision by movement across the field or by flickering of the stimulus. Additionally, the color of the target stimulus can be varied in order to increase the assessment parameters of the test. The size and shape of the target stimulus can also be varied in order to further assess the subject's visual field and to further test different parameters associated with the field of vision.

In addition to altering the color, size, and motion of the stimulus, the frequency and intensity of the visual stimulus can be altered in order to add to the test parameters of the apparatus 20.

The subject's responses to the visual stimuli projected onto the visor or screen 28 are recorded and analyzed by the computer 30 thus allowing for the calculation of the exact anatomical point on the subject's retina which was stimulated by the visual stimulus thereby allowing for the generation of an exact anatomical map of the subject's retina in which the exact part of the neural bands stimulated or not stimulated during the course of testing can be defined. By utilizing the apparatus 20 and method of the present invention, the visual field, including the peripheral vision of a subject 22, can be accurately mapped and examined.

In order to generate the map of the retina based on the subject's natural eye reflex to move the eye toward a stimulus entering the visual field, the computerized system 30 includes programming which is capable of integrating the record of eye movement with the light stimulus in order to generate a representative map showing healthy or damaged areas of the retina. The data generated and integrated by the apparatus 20 of the present invention can generate an exact topographical map of the retina that can be projected onto a previous record image of the fundus and create a real map of the damaged or undamaged areas of the retina. The fundus image can be stored in the computer 30 prior to the visual field test and can be integrated by the programming in creating the final map. That is, the fundus image of a patient taken by a fundus camera can be stored or recorded on a disk and the visual field map can be projected fundus image.

The apparatus 20 of the present invention can be used in ophthalmology for detecting maladies such as malfunctions of the external ocular muscles or in tests for detecting paralytic or paretic ocular nerves. The apparatus 20 can also be used in a binocular function evaluation or "squint" evaluation. For this type of evaluation, the apparatus 20 would be configured to generate and record "simultaneous" eye movement and alignment measurements from both eyes which will allow for the detection of the existence of squint in newborns, babies, or young children and thus will be a valuable screening tool.

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

REFERENCES CITED

Eye Tracking Systems Handbook from the Applied Science Laboratories Company, Bedford, Mass.

I claim:

1. An apparatus (20) for evaluating the visual field of an eye of a human (22), said apparatus (20) comprising;
    affixation means (24) for affixing a portion of said apparatus (20) to the eye of a human(22);
    eye tracking means (26) operatively connected to said affixation means (24) for tracking the position and location of the eye during movement of the eye of the human (22); and
    visual field stimulus generating means (28) operatively connected to said affixation means (24) for generating a visual stimulus whereby the anatomical point of the retina which is stimulated is determined to map the visual field of the eye of the human.

2. An apparatus (20) as set forth in claim 1 including data collection and analysis means (30) operatively connected to said apparatus (20) for collecting and analyzing data generated by said apparatus (20).

3. An apparatus (20) as set forth in claim 2 further including an at least two-way transmission means (32) operatively connected to said data generating, collection, and analysis means (30), to said eye tracking means (26), and to said visual field stimulus generating means (28) for recording eye movements of the human 22 and transmitting input to said visual field stimulus generating means (28).

4. An apparatus (20) as set forth in claim 2, wherein said data collection and analysis means (30) is a computer.

5. An apparatus (20) as set forth in claim 1, wherein said visual field stimulus generating means (28) includes a screen.

6. A method for examining a visual field of an eye of a human, said method including the steps of:
    stimulating the human eye movement reflex to an off field visual stimulus and mapping the human visual field based on positive reflex to the stimulus, said mapping step being defined as generating an anatomical map of the human's retina.

7. A method as set forth in claim 6, wherein said stimulating step includes a light source for generating the visual stimulus.

8. A method as set forth in claim 7, wherein the light source includes a colored light source.

9. A method as set forth in claim 7, wherein the light source is capable of generating a visual stimulus of various sizes and shapes.

10. A method as set forth in claim 7, wherein the light source is capable of generating different frequencies of light.

11. A method as set forth in claim 7, wherein the light source is capable of generating different intensities of light.

12. A method as set forth in claim 6, wherein said stimulating step further includes the step of moving the visual stimulus in and out of the human visual field.

13. A method as set forth in claim 6, wherein said stimulating step further includes the step of measuring peripheral vision of the eye of the human.

14. A method as set forth in claim 6, wherein said mapping step is further defined as calculating the exact anatomical point on the retina stimulated by the visual stimulus.

* * * * *